United States Patent [19]

Tsang et al.

[11] Patent Number: 4,556,748

[45] Date of Patent: Dec. 3, 1985

[54] PROCESS FOR PRODUCING ALKYLENE GLYCOLS

[75] Inventors: Albert C. Tsang, Baton Rouge, La.; Thomas L. Holland, Charlottesville, Va.; Johnny W. Masey, Baton Rouge, La.

[73] Assignee: The Dow Chemical Company, Midland, Mich.

[21] Appl. No.: 546,790

[22] Filed: Oct. 31, 1983

[51] Int. Cl.$^4$ .............................................. C07C 27/02
[52] U.S. Cl. ..................................... 568/858; 422/193
[58] Field of Search ........................................ 568/858

[56] References Cited

U.S. PATENT DOCUMENTS 3,629,343 12/1971 Levin et al. .
3,964,980 6/1976 Ozero ..................................... 203/42
4,066,706 1/1978 Schmidt .
4,117,250 9/1978 Foster et al. ......................... 568/858

OTHER PUBLICATIONS

Groggins, Unit Processes in Organic Synthesis (1958), 790–793.
McCrady, Patent Office Practice (1959), Sec. 88, 123–126.

*Primary Examiner*—Bernard Helfin
*Attorney, Agent, or Firm*—Paul D. Hayhurst

[57] ABSTRACT

Prepare alkylene glycols by hydrolyzing alkylene carbonates under specific conditions, and a reactor specially designed therefor.

20 Claims, 2 Drawing Figures

PROCESS FOR PRODUCING ALKYLENE GLYCOLS

BACKGROUND OF THE INVENTION

The present invention relates to the production of 1,2-alkylene glycols by hydrolysis of the corresponding alkylene carbonates. More specifically, this invention relates to a catalytic, continuous method for the hydrolysis of alkylene carbonates.

The prior art regarding the production of alkylene glycols via hydrolysis is summarized in detail in U.S. Pat. No. 4,117,250. Said patent further describes a continuous process for the production of ethylene glycol or propylene glycols via the hydrolysis of ethylene carbonate or propylene carbonate, respectively.

SUMMARY OF THE INVENTION

In one aspect, the present invention is an improved reactor having a shell, an inlet means, an outlet means, and at least one partition, each partition having therein a plurality of orifices. The reactor is especially adapted for use in the production of alkylene glycols via the catalytic hydrolysis of alkylene carbonates.

In another aspect, the present invention is a process for the production of an alkylene glycol by catalytically hydrolyzing the corresponding alkylene carbonate under mild conditions in a reaction zone:

(1) from which evolved $CO_2$ is readily removed; and
(2) in which the temperature is controlled such that the temperature of the liquid phase increases as said liquid phase passes through the reaction zone.

DETAILED DESCRIPTION OF THE INVENTION

Figure 1:
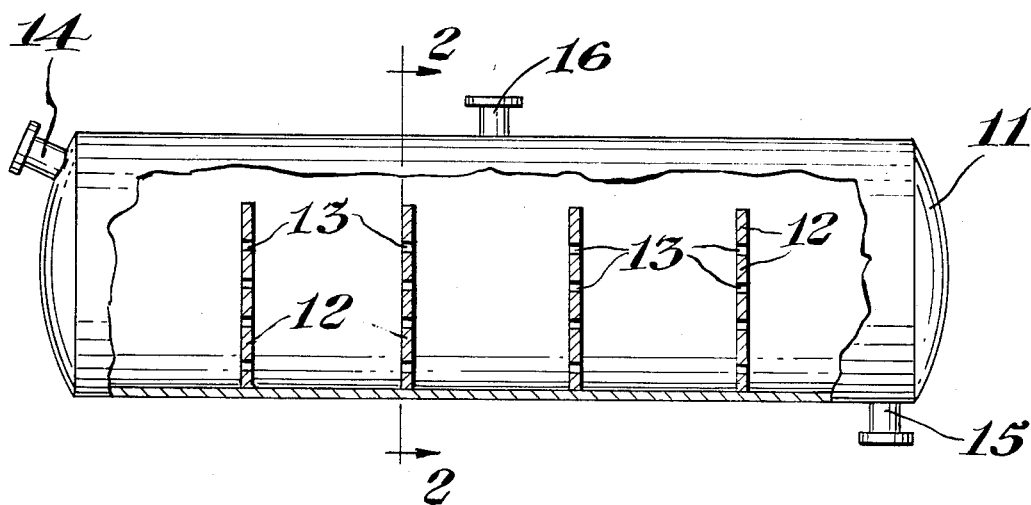
FIG. 1 is a side elevation, with partial cutaway, of a preferred embodiment of the reactor of the present invention.
Figure 2:
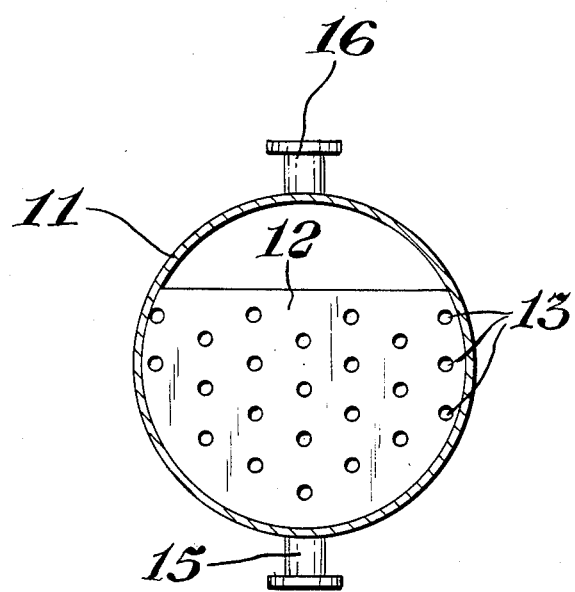
FIG. 2 is a cross-section taken at line 2—2 of FIG. 1.

Referring particularly to FIGS. 1 and 2, the reactor of a preferred embodiment of the present invention includes a shell 11 which defines a closed cylindrical vessel. The shell further contains at least one partition. For example, the reactor of FIG. 1 has 4 partitions 12 which are oriented in substantially parallel planes, said planes being substantially perpendicular to the longitudinal axis of the reactor. The partitions have perimeters which are less than the perimeter of the inner perimeter of the shell. Each partition has therein a plurality of small orifices 13 which allow a liquid phase reaction mixture to flow through each partition. It is desirable to employ at least two partitions. Preferably, at least 4 partitions are employed, and it is beneficial to employ at least about 20 partitions. The reactor is equipped with a means 14 for introducing liquids to the interior thereof, a means 15 for allowing liquids in the interior thereof to be removed, and a means 16 for allowing vapors in the interior thereof to be removed.

Typically, a mixture of water, catalyst, and an alkylene carbonate are introduced into the reactor via inlet means 14 in a continuous manner. The level of the liquid phase typically is maintained below the top of the partitions. Hydrolysis of the alkylene carbonate occurs in said mixture, and $CO_2$ is formed. The upper section of the reactor, i.e. that section which is above the top of the partitions 12, is sufficiently open to allow gaseous $CO_2$ to be removed readily from the reactor via the vapor outlet means 16. As the liquid phase flows through the reactor, the concentration of alkylene glycol increases, while the amount of $CO_2$ produced tends to decrease. Preferably, heat is supplied to the liquid phase as it approaches the reactor liquid outlet means 15. This heat may be supplied by any conventional means such as, for example, by a jacket on the shell 11 of the reactor or by heating coils (not shown) disposed between the partitions 12. The heat is supplied in a manner such that the temperature in the liquid phase increases as it passes through the reactor. The liquid phase is removed when it reaches the liquid outlet means 15.

The reactor of the present invention makes it possible to employ varying liquid levels in the reactor. This has the advantage of giving the operator maximum flexibility with respect to setting residence time. It should be noted that the process of the present invention may be employed with reactors other than that claimed herein.

The process of the present invention is an improved method for continuously producing an alkylene glycol by the hydrolysis of the corresponding alkylene carbonate. The process has many advantages compared to similar, known methods. An advantage may be realized in reduced pressure of operation, in reduced reaction time, in increased process flexibility, in reduced energy requirements, in reduced catalyst level, in lack of a requirement for catalyst recycle, or in any combination of these. Importantly, the process of the present invention may be employed to produce ethylene glycol which, after the catalyst and water are removed therefrom, can be used as Fiber Grade ethylene glycol. For an example of typical specifications for "Fiber Grade" or polyester grade ethylene glycol see U.S. Pat. No. 4,314,945 which is incorporated herein by reference. It should be noted that the specifications vary for "Fiber Grade" ethylene glycol depending on several commercial factors, and on the specific application for which the glycol is being obtained.

An alkylene carbonate is employed in the process of the present invention. Examples of suitable alkylene carbonates include ethylene carbonate, propylene carbonate, butylene carbonate, phenylene carbonate, and vinylene carbonate. Preferred alkylene carbonates are represented generally by the formula:

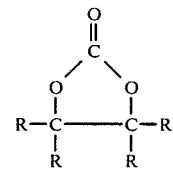

wherein each R is independently H or lower alkyl. Preferably, R is H or methyl. Most preferably, R is H. Propylene carbonate is a more preferred alkylene carbonate, and ethylene carbonate is most preferred.

The initial mole ratio of water to alkylene carbonate which is employed in the hydrolysis reaction may be any amount of water which is sufficient to react with all of the alkylene carbonate. Typically, at least a stoichiometric amount of water is employed, i.e., at least one mole of water per mole of alkylene carbonate is employed. However, from a practical standpoint, in order to achieve the kind of performance characterized for the process of this invention, one should employ at least about 1.2 moles of water and at most about 10 moles of water per each mole of alkylene carbonate. Preferably, from about 1.5 to about 2.5 moles of water will be employed per mole of alkylene carbonate. For example, when the molar ratio is below about 1.2, it becomes very difficult in the hydrolysis of ethylene carbonate to produce polyester grade ethylene glycol. Additionally, molar ratios below 1.2 make it difficult to minimize the production of unwanted by-products such as di- and triethylene glycols.

Advantageously, a catalyst is employed in the process of the present invention. Suitable catalysts include potassium compounds which, when incorporated into a protic medium under carbon dioxide pressure, produce potassium carbonate or potassium bicarbonate. Preferably, potassium carbonate is employed as the catalyst. Certain precautions should be taken when not using potassium carbonate as the catalyst. These precautionary measures are detailed in U.S. Pat. No. 4,117,250 at columns 5 and 6. The teachings of said patent with respect to type of catalysts are incorporated herein by reference.

A catalytic amount of the catalyst is employed in the process of the present invention. Typically, the amount of catalyst employed may range between about 0.001 and 10 weight percent, based on the weight of alkylene carbonate fed to the reactor. Preferably, the amount of catalyst is from about 0.01 to about 1 weight percent, and most preferably the amount of catalyst employed ranges from about 0.05 to about 0.2 weight percent. For the purposes of the present invention, the catalyst concentration is expressed in terms of potassium carbonate.

The process of the present invention may be conducted at any temperature and pressure at which an alkylene carbonate may be hydrolyzed to form an alkylene glycol. Typically the temperature ranges from about 90° C. to about 200° C. Preferably, the temperature ranges from about 120° C. to about 160° C. Typically, the pressure employed in the process of the present invention ranges from about 0 psig to about 200 psig. Preferably, the pressure in the reactor is from about 25 to about 80 psig. Advantageously, the process of the present invention may be carried out at less than 80 psig, which is the lower limit recited in U.S. Pat. No. 4,117,250, thus resulting in cost savings. Higher pressures typically will reduce the reaction rate but will simultaneously reduce the heat loads required to maintain the temperature of the reaction.

The process of the present invention additionally embodies the discovery that separation of carbon dioxide from the reaction mixture is an important way of increasing the speed of the reaction. Thus, higher pressures, which increase the solubility of $CO_2$, are less favored than are lower pressures.

The process of the present invention employs a reactor in which the temperature in the reaction zone is controllable such that the temperature of the liquid phase can be increased as said liquid phase passes through the reaction zone. This increasing temperature profile is preferred, and advantageous in that it drives the reaction to completion in the latter stages of the reactor while simultaneously minimizing the loss of water in the initial stages of the reactor thereby reducing energy costs associated with vaporization and subsequent condensation of water which may leave the reactor through the vapor outlet means. The temperature profile may be affected by using any known method of controlling the temperature of the liquid phase in a reactor. Relatedly, it should be noted that a pressure which is too low will lead to excessive evaporation of water which will increase the energy cost related to the subsequent condensation of the vaporized water.

When the water, alkylene carbonate and catalyst are combined in the manner described hereinabove, a product mixture is formed comprising the alkylene glycol which corresponds to the specific alkylene carbonate starting material. For example, ethylene carbonate is used to prepare ethylene glycol, and propylene carbonate is used to prepare propylene glycol.

SPECIFIC EMBODIMENTS

The following examples are given to illustrate the invention and should not be construed as limiting its scope. All parts and percentages are by weight unless otherwise indicated.

EXAMPLE 1

A reactor similar to that shown in FIGS. 1 and 2 is continuously supplied with ethylene carbonate, water and potassium carbonate. The feed rates of ethylene carbonate, water and potassium carbonate are approximately 30.6, 10.4 and 0.02 pounds per hour, respectively. The ethylene carbonate is premixed with a solution of potassium carbonate in water, and the homogeneous solution which is formed is then fed to the reactor through inlet 14 of FIG. 1. The temperature in the reactor is progressively increased from about 30° C. at the inlet 14, to 153° C. at the outlet 15. The reaction is carried out in five stages, i.e., the reactor has 4 partitions. The temperature is 126.6° C., 138.7° C., 147.8° C., 153° C. and 153° C. in stages 1, 2, 3, 4 and 5, respectively. Each reaction stage is separated from the other stages by the partitions 12. The pressure is 35 pounds per square inch gauge (psig). The total residence time in the reactor is 7.2 hours. The overall conversion of ethylene carbonate to ethylene glycol for each stage is 63.2, 89.3, 98.97, 99.93 and 100 percent, respectively. The composition of the stream leaving the reactor through outlet 15 is approximately 83, 17 and 0.075 percent by weight ethylene glycol, water and potassium carbonate, respectively.

Many modifications will suggest themselves to those skilled in the art but it is to be clearly understood that the present invention is not to be limited to the method of operation and precise details of construction as shown herein. Many changes may be made without departing from the spirit of the invention, or exceeding the scope of the appended claims. For example, it is contemplated to have partitions which extend fully from the bottom to the top of the reactor. It is further contemplated that such partitions would have openings therein which would be large enough to permit free vapor flow therethrough. It is further contemplated that the orifices in the partitions may be circular or rectangular or triangular or of any other shape which would permit free liquid flow therethrough. It is also contemplated that each partition could form a vapor barrier and that each enclosed section of the reactor would have its own vapor outlet means.

What is claimed is:

1. A process for the production of an alkylene glycol comprising contacting water and an alkylene carbonate under mild conditions at less than about 80 psig in the presence of a catalyst in a reaction zone;

(1) from which evolved $CO_2$ is readily removed; and
(2) in which the temperature is controlled such that the temperature of the liquid phase increases by at least about 26.4° C. as said liquid phase passes through the reaction zone.

2. The process of claim 1 wherein the alkylene carbonate is represented generally by the formula

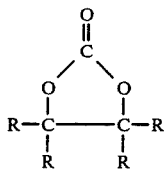

wherein each R is independently H or alkyl, and wherein the alkylene glycol is represented generally by the formula

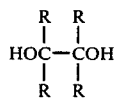

wherein R is as previously defined.

3. The process of claim 2 wherein each R is independently H or methyl.

4. The process of claim 3 wherein each R is independently H.

5. The process of claim 3 wherein the temperature in the reactor is from about 90° C. to about 200° C.

6. The process of claim 3 wherein the temperature in the reactor is from about 120° C. to about 160° C.

7. The process of claim 3 wherein the catalyst is potassium carbonate.

8. The process of claim 7 wherein the amount of catalyst employed is from about 0.001 to about 10 weight percent.

9. The process of claim 7 wherein the amount of catalyst employed is from about 0.01 to about 1 weight percent.

10. The process of claim 9 wherein the amount of catalyst employed is from about 0.05 to about 0.2 weight percent.

11. The process of claim 1 wherein at least about 1.2 moles of water are employed per mole of alkylene carbonate.

12. A process for the production of an alkylene glycol comprising contacting water and an alkylene carbonate under mild conditions in the presence of a catalyst in a reaction zone:
(1) from which $CO_2$ is readily removed; and
(2) in which the temperature is controlled such that the temperature of the liquid phase increases by at least about 26.4° C. as said liquid passes through the reaction zone;
the reaction zone being defined by a reaction vessel comprising:
(a) a shell;
(b) at least one partition, each partition having therein a plurality of orifices;
(c) an inlet means; and
(d) an outlet means.

13. A process of claim 12 wherein the outlet means comprises a means for vapor outlet and a means for liquid outlet.

14. A process of claim 13 wherein the vessel shell is oriented substantially horizontally.

15. A process of claim 14, the vessel having at least two partitions.

16. A process of claim 15 wherein the vessel partitions are oriented in substantially parallel planes which planes are substantially perpendicular to the longitudinal axis of the vessel.

17. A process of claim 16 wherein the perimeter of the partitions is less than the inner perimeter of the shell thereby providing an open vapor space.

18. A process of claim 15, the vessel having at least about 4 partitions.

19. A process of claim 18, the vessel having at least about 20 partitions.

20. A process of claim 16, the vessel further comprising a heating means by which heat may be supplied individually to various zones along the longitudinal axis of the vessel.

* * * * *